United States Patent [19]

Jongenburger

[11] Patent Number: 5,639,355
[45] Date of Patent: Jun. 17, 1997

[54] METHOD FOR ENHANCING THE YIELD OF TERTIARY BUTYL ALCOHOL IN A TERTIARY BUTYL ALCOHOL RECOVERY PROCESS

[75] Inventor: Huibert Sybrandus Jongenburger, Houston, Tex.

[73] Assignee: Texaco Chemical Inc., White Plains, N.Y.

[21] Appl. No.: 403,021

[22] Filed: Mar. 13, 1995

[51] Int. Cl.$^6$ .................................................. B01D 3/00
[52] U.S. Cl. ......................... 203/78; 203/79; 203/80; 568/697; 568/699; 568/913
[58] Field of Search .................. 203/42, 79–80, 203/78, 39, 73, 14, 18, DIG. 23, DIG. 16, DIG. 9; 568/691, 913, 699, 698; 549/529

[56] References Cited

U.S. PATENT DOCUMENTS

| | | | |
|---|---|---|---|
| 4,144,138 | 3/1979 | Rao et al. | 203/71 |
| 4,155,945 | 5/1979 | Levine | 585/639 |
| 4,296,262 | 10/1981 | Grane et al. | 568/910 |
| 4,902,385 | 2/1990 | Osterburg | 203/85 |
| 5,243,091 | 9/1993 | Kruse et al. | 568/699 |
| 5,250,156 | 10/1993 | Pucci et al. | 203/77 |
| 5,292,964 | 3/1994 | Gupta | 568/697 |
| 5,354,912 | 10/1994 | Hwan et al. | 568/697 |
| 5,414,145 | 5/1995 | Sheu et al. | 568/671 |

*Primary Examiner*—Virginia Manoharan
*Attorney, Agent, or Firm*—James L. Bailey; Harold J. Delhommer; Henry H. Gibson

[57] ABSTRACT

A tertiary butyl hydroperoxide reaction product is distilled to provide a tertiary butyl alcohol distillation fraction containing tertiary butyl alcohol and a heavier fraction containing unreacted tertiary butyl hydroperoxide, and reaction by-products boiling below tertiary butyl alcohol, the tertiary butyl alcohol fraction is charged to a vacuum distillation column for separation into a vaporized overhead tertiary butyl alcohol fraction that is cooled to obtain a liquefaction product containing a minor amount of vaporized tertiary butyl alcohol and a major amount of a liquified tertiary butyl alcohol, and the tertiary butyl alcohol vapors are dissolved in water to form an aqueous solution of tertiary butyl alcohol from which the tertiary butyl alcohol is recovered.

9 Claims, 1 Drawing Sheet

METHOD FOR ENHANCING THE YIELD OF TERTIARY BUTYL ALCOHOL IN A TERTIARY BUTYL ALCOHOL RECOVERY PROCESS

BACKGROUND OF THE INVENTION

1. Field of the Invention

This invention relates to the recovery of tertiary butyl alcohol. More particularly, this invention relates to a method for enhancing the yield of tertiary butyl alcohol during a tertiary butyl alcohol recovery process. Still more particularly, this invention relates to a method for the manufacture and recovery of tertiary butyl alcohol wherein an enhanced yield of tertiary butyl alcohol is obtained during the recovery process.

2. Background Information

Tertiary butyl alcohol can be recovered by distillation from a tertiary butyl hydroperoxide reaction product comprising oxygen-containing compounds, including tertiary butyl alcohol, unreacted tertiary butyl hydroperoxide, oxygen-containing by-products such as ditertiary butyl peroxide, allyl tertiary butyl peroxide, isopropyl hydroperoxide, etc. and water.

Methyl tertiary butyl ether (MTBE) can be prepared by the catalytic reaction of tertiary butyl alcohol (TBA) with methanol. Normally, an excess of methanol is used.

It is known that tertiary butyl alcohol and propylene oxide can be prepared by the molybdenum-catalyzed reaction of propylene with tertiary butyl hydroperoxide.

3. Prior Art

Kollar U.S. Pat. No. 3,351,635 discloses the reaction of tertiary butyl hydroperoxide with propylene to provide a reaction product comprising unreacted propylene, propylene oxide, and tertiary butyl alcohol. Related processes are disclosed, for example, in Marquis et al U.S. Pat. No. 4,845,251 and Marquis et al U.S. Pat. No. 4,891,437.

Grane et al. U.S. Pat. No. 4,296,262 is representative of patents directed to the manufacture and recovery of tertiary butyl alcohol by the thermal decomposition of tertiary butyl hydroperoxide.

Grane et al. U.S. Pat. No. 4,294,999 and Sanderson et al. U.S. Pat. No. 4,922,036 are representative of patents directed to the manufacture and recovery of tertiary butyl alcohol by the catalytic decomposition of tertiary butyl hydroperoxide.

Rao et al. U.S. Pat. No. 4,144,138, Kruse et al. U.S. Pat. No. 5,243,091, Knifton et al. U.S. Pat. No. 4,822,921 and Gupta U.S. Pat. No. 5,292,964, are representative of patents directed to the manufacture and recovery of methyl tertiary butyl ether by the catalytic reaction of methanol with tertiary butyl alcohol.

In all of these processes a tertiary butyl hydroperoxide reaction product is obtained comprising tertiary butyl alcohol, unreacted tertiary butyl hydroperoxide and reaction products boiling below tertiary butyl alcohol, such as water, ditertiary butyl peroxide, tertiary butyl hydroperoxide, allyl tertiary butyl peroxide, etc.

It is conventional to recover tertiary butyl alcohol from a tertiary butyl hydroperoxide reaction product by distillation in a distillation zone comprising a plurality of distillation columns, including a vacuum distillation column to which a tertiary butyl alcohol fraction is charged and in which it is separated into a vaporized overhead tertiary butyl alcohol fraction and a lower boiling liquid fraction comprising unreacted tertiary butyl hydroperoxide and reaction by-products boiling below tertiary butyl alcohol.

SUMMARY OF THE PRESENT INVENTION

In accordance with the present invention, a tertiary butyl hydroperoxide reaction product is distilled to provide a tertiary butyl alcohol distillation fraction comprising tertiary butyl alcohol, unreacted tertiary butyl hydroperoxide, and reaction by-products boiling below tertiary butyl alcohol.

The tertiary butyl alcohol fraction is charged to a vacuum distillation column and separated into a vaporized overhead tertiary butyl alcohol fraction and a lower boiling liquid fraction comprising unreacted tertiary butyl hydroperoxide, and reaction by-products boiling below tertiary butyl alcohol.

The vaporized overhead fraction is cooled to obtain a liquefaction product comprising a minor amount of vaporized tertiary butyl alcohol and a major amount of a liquified tertiary butyl alcohol.

The tertiary butyl alcohol vapors are dissolved in water to form an aqueous solution of tertiary butyl alcohol, and tertiary butyl alcohol is recovered from the aqueous solution of tertiary butyl alcohol to thereby obtain an enhanced yield of tertiary butyl alcohol.

DETAILED DESCRIPTION OF THE PRESENT INVENTION

In accordance with a preferred embodiment of the present invention, a distillation zone is provided which may comprise one or more pressure distillation columns and a vacuum distillation column of the type wherein a vacuum is maintained, for example, by an overhead vacuum pump connected to a vacuum distillation column reflux drum by a vent line; wherein the tertiary butyl hydroperoxide reaction product is separated by atmospheric distillation to provide one or more lighter distillation fractions and a heavier tertiary butyl alcohol fraction comprising tertiary butyl alcohol, unreacted tertiary butyl hydroperoxide, and reaction products boiling below tertiary butyl alcohol, wherein the tertiary butyl alcohol fraction is charged to the vacuum distillation column and separated into a vaporized overhead tertiary butyl alcohol fraction and a lower boiling liquid fraction comprising unreacted tertiary butyl hydroperoxide, and reaction by-products boiling below tertiary butyl alcohol; wherein the vaporized overhead fraction is cooled to obtain a liquefaction product comprising a minor amount of vaporized tertiary butyl alcohol and a major amount of a liquified tertiary butyl alcohol wherein the tertiary butyl alcohol vapors are dissolved in water to form an aqueous solution of tertiary butyl alcohol, and wherein tertiary butyl alcohol is recovered from the aqueous solution of tertiary butyl alcohol to thereby obtain an enhanced yield of tertiary butyl alcohol.

In accordance with a second embodiment of the present invention, tertiary butyl hydroperoxide is reacted with propylene in a reaction zone to provide a first reaction product comprising by-products boiling below tertiary butyl alcohol, unreacted propylene, propylene oxide, tertiary butyl alcohol, unreacted tertiary butyl hydroperoxide, and by-products boiling above tertiary butyl alcohol;

a distillation zone is provided comprising a first atmospheric pressure distillation column, a second atmospheric pressure distillation column and a third vacuum distillation column of the type wherein, for example, a vacuum is maintained by an overhead vacuum pump connected with a vacuum distillation column reflux drum by a vent line;

the tertiary butyl hydroperoxide reaction product is charged to the first distillation column and separated therein into a first lighter propylene recycle fraction and a first heavier fraction;

the first heavier fraction is charged to the second distillation column and separated therein into a second lighter propylene oxide fraction and a second heavier tertiary butyl alcohol fraction comprising tertiary butyl alcohol, unreacted tertiary butyl hydroperoxide, and reaction products boiling below tertiary butyl alcohol;

the second tertiary butyl alcohol fraction is charged to the vacuum distillation column and separated therein into a vaporized overhead tertiary butyl alcohol fraction and a lower boiling liquid fraction comprising unreacted tertiary butyl hydroperoxide, and reaction products boiling below tertiary butyl alcohol;

the vaporized overhead fraction is cooled to obtain a liquefaction product comprising a minor amount of vaporized tertiary butyl alcohol and a major amount of a liquified tertiary butyl alcohol;

the liquefaction product is charged to the reflux drum;

liquified tertiary butyl alcohol is removed from the reflux drum, and split to provide a reflux stream for the vacuum distillation column and a recovered liquified tertiary butyl alcohol stream;

the minor amount of vaporized tertiary butyl alcohol is removed from the reflux drum through a vent line and dissolved therein, with water to form an aqueous solution of tertiary butyl alcohol; and tertiary butyl alcohol is recovered from the aqueous solution of tertiary butyl alcohol to thereby obtain an enhanced yield of tertiary butyl alcohol.

In accordance with a third embodiment of the present invention, tertiary butyl hydroperoxide is decomposed to provide a tertiary butyl hydroperoxide reaction product comprising by-products boiling below tertiary butyl alcohol, tertiary butyl alcohol, unreacted tertiary butyl hydroperoxide, and by-products boiling below tertiary butyl alcohol, the tertiary butyl hydroperoxide reaction product is separated in a first distillation zone into a lighter boiling fraction comprising reaction products boiling above tertiary butyl alcohol and a heavier boiling tertiary butyl alcohol distillation fraction comprising tertiary butyl alcohol, unreacted tertiary butyl hydroperoxide, and reaction products boiling below tertiary butyl alcohol, the higher boiling tertiary butyl alcohol fraction is charged to a vacuum distillation column and separated therein at subatmospheric pressure into a vaporized overhead tertiary butyl alcohol fraction and a higher boiling liquid fraction comprising unreacted tertiary butyl hydroperoxide and reaction by-products boiling below tertiary butyl alcohol, the vaporized overhead fraction is cooled to obtain a liquefaction product comprising a minor amount of vented vaporized tertiary butyl alcohol and a major amount of a liquified tertiary butyl alcohol, the vented tertiary butyl alcohol vapors are dissolved in water to form an aqueous solution of tertiary butyl alcohol, and tertiary butyl alcohol is recovered from the aqueous solution of tertiary butyl alcohol to thereby obtain an enhanced yield of tertiary butyl alcohol.

In accordance with a fourth embodiment of the present invention, the liquified tertiary butyl alcohol is recovered and reacted with methanol to provide a methyl tertiary butyl ether reaction product comprising methyl tertiary butyl ether, unreacted tertiary butyl alcohol, unreacted methanol and water, and the methyl tertiary butyl ether reaction product is fractionated in a methyl tertiary butyl ether distillation zone together with the aqueous solution of tertiary butyl alcohol to provide distillation fractions including a methyl tertiary butyl ether product fraction and a tertiary butyl alcohol fraction to thereby obtain an enhanced yield of tertiary butyl alcohol.

Preferably, in accordance with the fourth embodiment of the present invention, the methanol and tertiary butyl alcohol are reacted in an MTBE reaction zone to provide a methyl tertiary butyl ether reaction product which is fractionated in a distillation zone comprising a first distillation column, a second distillation column, and a third distillation column, the methyl tertiary butyl ether reaction product being fractionated in the first atmospheric distillation column to provide a lighter methyl tertiary butyl ether product fraction and a first heavier fraction. The first heavier fraction together with the aqueous solution of tertiary butyl alcohol obtained in the second or third embodiments is fractionated in the second distillation column to provide a lighter tertiary butyl alcohol fraction and a second heavier fraction, and the second heavier fraction is fractionated in the third atmospheric distillation column to provide a lighter methanol fraction and a heavier water fraction.

DESCRIPTION OF THE PREFERRED EMBODIMENT

Figure 1:
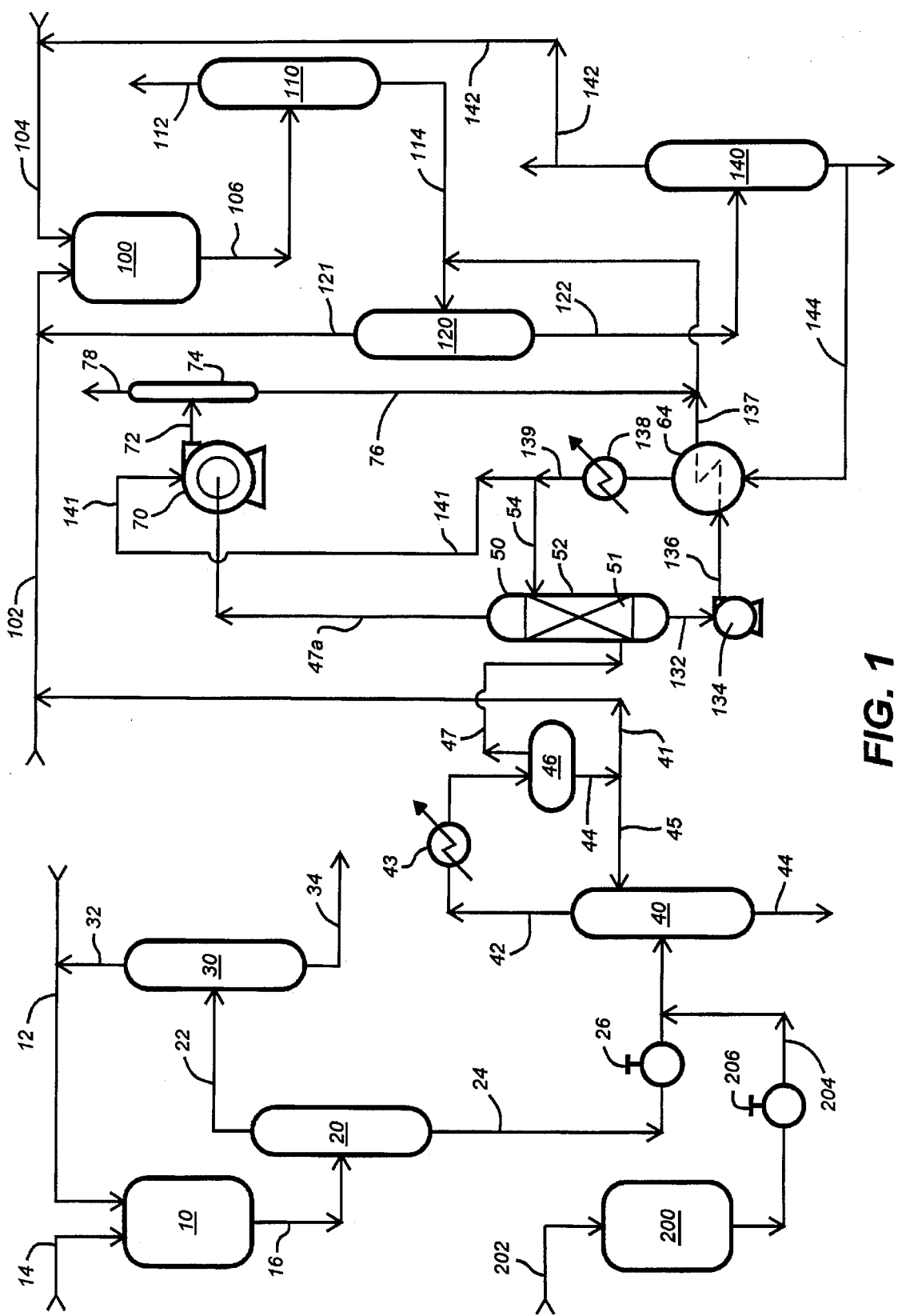
FIG. 1 is a schematic flow sheet which conventional parts omitted showing the general reaction and recovery sequence of the present invention for the manufacture and purification of tertiary butyl alcohol.

Turning now to the drawing, there is shown a schematic flow sheet illustrating a preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with one embodiment of the present invention, propylene is charged to reactor 10 by line 12. A solution of tertiary butyl hydroperoxide (TBPH) and a soluble molybdenum catalyst in tertiary butyl alcohol (TBA) is charged to reactor 10 by line 14. The epoxidation reaction product is discharged by line 16 leading to distillation column 20 where the epoxidation reaction product is separated into a propylene plus propylene oxide fraction 22 and a heavier fraction that is charged to a vacuum distillation column 40 by a line 24 controlled by a valve 26. In distillation column 30, the fraction 22 is separated into a heavier crude propylene oxide fraction 34 and a lighter fraction 32 comprising primarily propylene which is recycled to reactor 10 by line 12.

In accordance with another embodiment of the present invention, a solution of tertiary butyl hydroperoxide (TBPH) in tertiary butyl alcohol (TBA) is charged to reactor 200 by line 202 and tertiary butyl hydroperoxide decomposition conditions of time, temperature and pressure are established so as to convert a significant portion of the tertiary butyl hydroperoxide to tertiary butyl alcohol and water. A tertiary butyl hydroperoxide decomposition catalyst such as a soluble molybdenum catalyst may be used, if desired. If a catalyst is used, it is charged to reactor 200 in the tertiary butyl alcohol feedstock charged by the line 202.

The tertiary butyl hydroperoxide decomposition reaction product is discharged from the reactor 200 by a line 204 controlled by a valve 206 that leads to the charge line 24 for the vacuum distillation column 40.

It will be understood that only one of the valves 26 or 206 will be open and that the other valve will be closed and that only one of the reactors 10 and 200 will be operated at any given time.

The composition of the tertiary butyl hydroperoxide decomposition reaction product will be analogous in composition to the composition of the heavier fraction 34 in that the same reaction components in about the same proportions will be present. Thus, the vacuum distillation column 40 can be operated in essentially the same manner with either feedstock 24 or feedstock 204.

The vacuum distillation column 40 is operated so as to separate the feedstock charged thereto into a vaporized overhead tertiary butyl alcohol fraction 42 and a heavier fraction 44 comprising the remainder of the charge stock.

A subatmospheric pressure for the vacuum distillation column 40 is obtained by connecting the overhead line 42 of the vacuum distillation column 40 with a suitable device for generating a subatmospheric pressure, such as liquid ring vacuum pump 70.

Thus, for example, the vaporized overhead vacuum distillation product fraction 42 (which will primarily be comprised of tertiary butyl alcohol) may be passed through a heat-exchanger 43 where most of the overhead vapors will be condensed to provide a liquid tertiary butyl alcohol product and the resultant mixture of liquid and vapor may be charged to a reflux drum 46.

The condensed liquid comprising tertiary butyl alcohol is discharged from the reflux drum 46 by a line 44. A portion of the liquified tertiary butyl alcohol is returned to vacuum distillation column 40 as reflux by a line 45 and the remainder of the liquified tertiary butyl alcohol is recovered by line 41.

A vent line 47 is provided to interconnect the top of the reflux drum 46 with the liquid ring vacuum pump 70. A water absorption tower 50 is installed in the vent line 47 to absorb and recover vaporized tertiary butyl alcohol contained in the vapors withdrawn from the reflux drum 46 by the vent line 47.

The water absorption tower 50 may suitably comprise a tubular casing 51 in which a bed 52 of an inert packing such as rings or saddles is installed. Vapors from the vent line 47 are introduced adjacent the bottom of the casing. Water is introduced into the casing adjacent the top thereof by a line 54 for downward flow through the bed 52 in countercurrent contact with the ascending vapors charged by the line 47. Tertiary butyl alcohol vapors are absorbed in the downwardly flowing stream of water to form an aqueous solution of tertiary butyl alcohol that is discharged from the bottom of the tower 50 by a line 132. The ascending vapors are withdrawn from the top of tower 50 by an extension 47a of the vent line leading to the liquid ring vacuum pump 70.

The vapors charged to the liquid ring vacuum pump 70 by line 47a are predominantly composed of natural gas, air and small amounts of other hydrocarbons and unabsorbed tertiary butyl alcohol. They are discharged by a line 72 leading to drum 74 where the seal water is separated from the non-condensables and the water discharged by a line 76. Uncondensed, normally vapor components such as natural gas and air are discharged by a vent line 78.

The tertiary butyl alcohol in the aqueous solution of tertiary butyl alcohol that is discharged from the bottom of the tower 50 by line 132 may be recovered therefrom by distillation in any suitable manner. In accordance with a preferred embodiment of the present invention, a facility for the manufacture of methyl tertiary butyl ether from tertiary butyl alcohol and methanol is integrated with the tertiary butyl alcohol recovery process of the present invention. This permits a more economical recovery of the tertiary butyl alcohol in the aqueous solution of tertiary butyl alcohol that is discharged from the bottom of the tower 50 by line 132. When this is to be done, tertiary butyl alcohol is charged to a methyl tertiary butyl ether reactor 100 containing a bed of a suitable etherification catalyst, such as a cationic cross-linked sulfonated styrene/divinyl benzene resin by a charge line 102 and methanol is charged by a charge line 104 to reactor 100. Etherification reaction conditions are established in reactor 100 in order to provide a reaction product comprising methyl tertiary butyl ether, tertiary butyl alcohol, methanol and water. The reaction product is discharged from reactor 100 by a discharge line 106 leading to a distillation column 110 where the reaction product is separated into a lighter crude methyl tertiary butyl ether reaction product 112 and a heavier fraction 114. The heavier fraction 114 is charged to a distillation column 120 where it is separated into a lighter crude tertiary butyl alcohol fraction 121 that may be recycled to the tertiary butyl alcohol charge line 102 and a heavier fraction 122 comprising water and methanol.

The heavier fraction 122 is charged to a distillation column 140 where it is separated into an overhead methanol discharge fraction 142 that can be recycled to the methanol charge line 104, if desired, and a bottoms water fraction 144.

In accordance with the present invention, the aqueous solution of tertiary butyl alcohol that is discharged from the bottom of the tower 50 by line 132 is charged by pump 134 to a feed/effluent heat exchanger 64 and then by line 138 to the charge line 114 for the distillation column 120 so that it can be co-distilled with the fraction 114. When this is done, the tertiary butyl alcohol in the aqueous solution of tertiary butyl alcohol that is discharged from the bottom of tower 50 by the line 132 is charged to the distillation column 120 together with the heavier fraction 114 discharged from the distillation column 110 by the line 114. The combined streams 114 and 121 are distilled in the distillation column 120 to provide a lighter fraction 121 comprising tertiary butyl alcohol and a heavier fraction 122 comprising methanol and water. As was pointed out above, the aqueous solution of methanol discharged from distillation column 120 by the line 122 can be separated in distillation column 140 into a lighter methanol fraction 142 and a heavier water fraction 144.

In accordance with this modification, all or a part of the bottoms water fraction 144 is charged to the heat-exchanger 64 to heat the stream 136 before it is charged to the line 114. The fraction 144, after discharge from the heat exchanger 64 is further cooled in heat exchanger 138. The thus-cooled water fraction is discharged from heat exchanger 138 by a line 139, which is split into a line 54 leading to the absorber 50, and a line 140 leading the liquid seal of the liquid seal ring vacuum pump 70.

TBA contained in the vapor fraction 47 drawn to absorption tower 50 is absorbed in the water fraction 132 as it flows downwardly through absorption tower 50. The thus-formed solution of TBA in water is withdrawn from absorption tower 50 by a line 132 connected with a pump 134. The solution is discharged from the pump 134 by a line 136 leading to the feed/effluent heat exchanger 64 where it is heated by the stream 144. The heated solution is withdrawn from heat exchanger 64 by a line 137 leading to distillation column 120; the heated solution being charged to distillation column 120 by combining it with the feed fraction 114.

The fraction 122 is charged to a distillation column 140 where it is separated into a lighter methanol fraction 142 (that may be recycled to methanol charge line 104 by a recycle line 144 if desired) and a water fraction 144.

OPERATION

By way of example, propylene may be charged to reactor 10 by charge line 12. A solution of tertiary butyl hydroperoxide in tertiary butyl alcohol may be prepared containing from about 30 to 60 wt. % of tertiary butyl hydroperoxide and about 100 to 600 ppm of a soluble molybdenum catalyst, based on the combined weight of the propylene and tertiary butyl hydroperoxide. Any suitable soluble molybdenum catalyst may be used such as, for example, a catalyst of the type disclosed in Marquis et al. U.S. Pat. No. 4,626,596 or Marquis et al. U.S. Pat. No. 4,703,017. The solution is charged to reactor 10 by a charge line 14 in amount selected to provide a charge mole ratio of propylene to tertiary butyl hydroperoxide of from about 1 to about 3 moles of propylene per mole of tertiary butyl hydroperoxide. Epoxidation reaction conditions are established in the reactor 10 including, for example, a temperature of about 150° to about 350° F. and a pressure of about 500 to about 3,000 psig. The reaction time may suitably be from about 0.5 to 4 hours.

As a consequence, a tertiary butyl hydroperoxide reaction product is formed comprising unreacted propylene, propylene oxide, TBA, reaction by-products and water. The tertiary butyl hydroperoxide reaction product is discharged from the reactor 10 by a line 16 leading to a first distillation column 20 where the tertiary butyl hydroperoxide reaction product is separated into a first lighter distillation fraction 22 comprising the propylene and propylene oxide, and a first heavier fraction 24 comprising tertiary butyl alcohol, unreacted tertiary butyl hydroperoxide and reaction products boiling below tertiary butyl alcohol. Distillation conditions in the first distillation column 20 may include a top temperature of about 100°, a bottom temperature of about 250° F. and an operating pressure of about 70 to 130 psig (e.g., 110 psia).

The first lighter distillation fraction 22 is suitably charged to a distillation column 30 where it is separated into an overhead propylene recycle fraction 32 and a heavier propylene oxide fraction 34.

The first heavier fraction 24 is charged to a third vacuum distillation column 40 where the first heavier fraction is separated into a third lower boiling tertiary butyl alcohol fraction 42 and a fourth higher boiling fraction discharged by a line 44 comprising unreacted tertiary butyl hydroperoxide and reaction products boiling below tertiary butyl alcohol. Distillation conditions in the third distillation column 40 may include a top temperature of about 130° to about 140° F., a bottom temperature of about 160° to about 200° F. such as a temperature of about 160° to about 170° F. and an operating pressure of about 3 to 10 psia (e.g., 28 psia).

As indicated previously, subatmospheric distillation conditions are established in the vacuum distillation column 40, such as a subatmospheric pressure of about 3 to about 10 psia by operatively connecting the overhead line 42 of the vacuum distillation column 40 with a suitable device for generating a subatmospheric pressure, such as liquid ring vacuum pump 70. Within the vacuum distillation column 40, distillation conditions are established including, for example, a top temperature of about 120° to about 170° F. A heat-exchanger 43 is provided in the line 42 to cool the overhead vapors to a temperature of about 100° to about 110° F. so as to provide a mixed vapor/liquid tertiary butyl alcohol condensate that is charged to a reflux drum 46.

The liquified tertiary butyl alcohol is discharged from reflux drum 46 by a line 44. About 10 to about 30% of the liquified tertiary butyl alcohol in the line 46 is returned to vacuum distillation column 40 as reflux by line 45 and the remainder of the liquified tertiary butyl alcohol is recovered by line 41.

The vapor in the reflux drum, comprising about 40 to about 80 wt. % of tertiary butyl alcohol, is withdrawn from the reflux drum 46 by vent line 47 which leads to a charge point adjacent the bottom of the water extraction column 50. Simultaneously, water is charged to the water extraction column 50 adjacent the top thereof by a line 54. About 8 to about 12 times the amount of water, based on the weight of the tertiary butyl alcohol vapor charged to column 50 through line 47, is charged by line 54. As the vapors ascend the water extraction column 50, substantially all of the tertiary butyl alcohol contained therein is absorbed by the downflowing stream of water. The resultant aqueous solution of tertiary butyl alcohol, which may typically contain about 6 to about 10 wt. % of tertiary butyl alcohol is discharged from the water extraction column 50 by a line 132 leading to a pump 134 to be further processed in any suitable manner for the recovery of the tertiary butyl alcohol contained therein, such as in a manner to be describe hereafter.

The undissolved vapors, comprising mostly natural gas, air and other insoluble hydrocarbons are discharged by the line 47a leading to the liquid ring vacuum pump 70 and are discharged therefrom at about atmospheric pressure by a line 72 leading to drum 74 where the gaseous components separate from the seal water and are discharged by a line 78. The liquid ring vacuum pump seal water, containing any tertiary butyl alcohol not absorbed in column 50, is discharged by a line 76 and combined with the effluent from the column 50 in line 137.

In accordance with a preferred embodiment of the present invention, a methyl tertiary butyl ether manufacturing facility wherein tertiary butyl alcohol and methanol are used as feedstocks is operated together with the tertiary butyl alcohol recovery process of the present invention. When this is done, the tertiary butyl alcohol in the aqueous solution of tertiary butyl alcohol that is charged from the bottom of the tower 50 by line 132 to the pump 134 can be transported to the methyl tertiary butyl ether manufacturing facility for recovery therein.

When this is to be done, tertiary butyl alcohol is charged by a charge line 102 to a methyl tertiary butyl ether reactor 100 containing a bed of a suitable etherification catalyst, such as a cationic cross-linked sulfonated styrene/divinyl benzene resin and methanol is charged by a charge line 104 to reactor 100 in the molar ratio of about 1.1 to 3 mols of methanol per mol of tertiary butyl alcohol. Etherification reaction conditions are established in reactor 100, including for example a temperature of about 100° to about 300° F., and a pressure of about 50 to 500 psia. The feed mixture is suitably fed to the reactor 100 by the lines 102 and 104 at the rate of about 1 to about 4 volumes of feed mixture per volume of catalyst per hour in order to provide a reaction product comprising methyl tertiary butyl ether, tertiary butyl alcohol, methanol and water.

The reaction product is discharged from reactor 100 by a discharge line 106 leading to a distillation column 110 where the reaction product is fractionated under suitable distillation conditions such as a liquid reflux ratio of about one-half to about two, a distillation temperature of about 150° to about 250° F. and a pressure of about 15 to 60 psia into a lighter crude methyl tertiary butyl ether reaction product 112 and a heavier fraction 114.

The heavier fraction 114 is charged to a distillation column 120 where it is separated under suitable distillation conditions, such as a liquid reflux ratio of about one-half to about one, a distillation temperature of about 200° to about 400° F. and a pressure of about 110 to 160 psia into a lighter crude tertiary butyl alcohol fraction 121 and a heavier fraction 122 comprising water and methanol.

The heavier fraction 122 is charged to a distillation column 140 where it is separated under suitable distillation conditions such as a liquid reflux ratio of about one to about two, a distillation temperature of about 250° to about 350° F. and a pressure of about 120 to 170 psia into an overhead methanol fraction 142 that can be recycled to the methanol charge line 104, if desired, and a bottoms water fraction 144.

In accordance with the present invention, the aqueous solution of tertiary butyl alcohol that is discharged from the bottom of the tower 50 by line 132 is charged by pump 134 to a feed/effluent heat exchanger 136 and then by line 137 to the charge line 114 for the distillation column 120 so that it can be co-distilled with the fraction 114. The aqueous solution of tertiary butyl alcohol discharged from the drum 74 by the line 76 is also charged to the distillation column 120 by the lines 138 and 114 for co-distillation with the fraction 114. When this is done, the tertiary butyl alcohol in the aqueous solution of tertiary butyl alcohol that is discharged from the bottom of the tower 50 by line 132 and the tertiary butyl alcohol in the aqueous solution of tertiary butyl alcohol that is discharged from the bottom of drum 74 by line 76 are recovered by way of line 121 for recycle to the methyl tertiary butyl ether reactor 100. Water and methanol are discharged from the distillation column 120 by line 122.

All or a part of the bottoms water fraction 144 from column 140 may be charged to the heat-exchanger 136 to heat the stream 136. The fraction 144, after discharge from the heat exchanger 64 is further cooled in heat exchanger 138. The thus-cooled water is discharged from heat exchanger 138 by a line 139 and split in a major fraction leading to the tower 50 by line 54 and a minor fraction leading to the liquid seal ring vacuum pump 70 by a line 140.

Having thus described my invention, what is claimed is:

1. In a method wherein a tertiary butyl alcohol fraction comprising tertiary butyl alcohol, unreacted tertiary butyl hydroperoxide, and reaction by-products boiling below tertiary butyl alcohol, is charged to a vacuum distillation column and separated into a vaporized overhead tertiary butyl alcohol fraction and a lower boiling liquid fraction comprising unreacted tertiary butyl hydroperoxide, and reaction by-products boiling below tertiary butyl alcohol, the improvement which comprises:
condensing the overhead vaporized overhead fraction to obtain a liquefaction product comprising a minor amount of vaporized tertiary butyl alcohol and a major amount of a liquified tertiary butyl alcohol,
dissolving the tertiary butyl alcohol vapors in water to form an aqueous solution of tertiary butyl alcohol, and
charging said aqueous solution of tertiary butyl alcohol to a distillation column and separating it therein at a liquid reflux ratio of about one-half to one at an elevated temperature of about 200° to about 400° F. and pressure of about 110 to about 160 psia into a lighter tertiary butyl alcohol fraction and a heavier water fraction.

2. A method as in claim 1 wherein said vacuum distillation column is operated under distillation conditions including a top temperature of about 130° to about 140° F., a bottoms temperature of about 160° to about 170° F. and a pressure of about 3 to about 10 psia.

3. A method as in claim 1 wherein a portion of the liquified tertiary butyl alcohol is returned to said vacuum distillation column reflux, wherein the remainder of the liquified tertiary butyl alcohol is reacted with methanol to provide a methyl tertiary butyl ether reaction product comprising methyl tertiary butyl ether, unreacted tertiary butyl alcohol, unreacted methanol;

wherein said aqueous solution of tertiary butyl alcohol is distilled in admixture with a heavier methyl tertiary butyl ether reaction product fraction to provide distillation fractions including a methanol fraction and a tertiary butyl alcohol fraction.

4. In a method wherein tertiary butyl hydroperoxide is decomposed to provide a tertiary butyl hydroperoxide reaction product comprising by-products boiling above tertiary butyl alcohol, tertiary butyl alcohol, unreacted tertiary butyl hydroperoxide, and by-products boiling below tertiary butyl alcohol, wherein said tertiary butyl hydroperoxide reaction product is separated in a first distillation zone into a lighter boiling fraction comprising reaction products boiling above tertiary butyl alcohol and a higher boiling tertiary butyl alcohol distillation fraction comprising tertiary butyl alcohol, unreacted tertiary butyl hydroperoxide, and reaction products boiling below tertiary butyl alcohol, the improvement which comprises:
charging said higher boiling tertiary butyl alcohol fraction to a vacuum distillation column and separated therein at subatmospheric pressure into a vaporized overhead tertiary butyl alcohol fraction and a higher boiling liquid fraction comprising unreacted tertiary butyl hydroperoxide, and reaction by-products boiling below tertiary butyl alcohol,
partially condensing said vaporized overhead tertiary butyl alcohol fraction to provide a liquid tertiary butyl alcohol product and a vented product comprising vaporized tertiary butyl alcohol,
dissolving the vented tertiary butyl alcohol vapors in water to form an aqueous solution of tertiary butyl alcohol, and
charging said aqueous solution of tertiary butyl alcohol to a distillation column and separating it therein at a liquid reflux ratio of about one-half to one at an elevated temperature of about 200° to about 400° F. and pressure of about 110 to about 160 psia into a lighter tertiary butyl alcohol fraction and a heavier water fraction.

5. A method as in claim 4 wherein said vacuum distillation column is operated under distillation conditions including a top temperature of about 130° to about 140° F., a bottoms temperature of about 160° to about 170° F., and a pressure of about 3 to about 10 psia.

6. In a method wherein tertiary butyl hydroperoxide is reacted with propylene to provide a tertiary butyl hydroperoxide reaction product comprising by-products boiling below tertiary butyl alcohol, unreacted propylene, propylene oxide, tertiary butyl alcohol, unreacted tertiary butyl hydroperoxide, and by-products boiling above tertiary butyl alcohol, wherein said tertiary butyl hydroperoxide reaction product is separated in a first distillation zone into a first lighter boiling fraction comprising propylene and propylene oxide and a second higher boiling fraction comprising tertiary butyl alcohol, unreacted tertiary butyl hydroperoxide, and reaction products boiling below tertiary butyl alcohol, the improvement which comprises:

charging said second higher boiling tertiary butyl alcohol fraction to a vacuum distillation column and separated therein at subatmospheric pressure into a vented vaporized overhead tertiary butyl alcohol fraction and a lower boiling liquid fraction comprising unreacted tertiary butyl hydroperoxide, and reaction by-products boiling below tertiary butyl alcohol, condensing said vaporized overhead fraction to obtain a liquefaction product comprising a minor amount of vented vaporized tertiary butyl alcohol and a major amount of a liquified tertiary butyl alcohol, dissolving the vented tertiary butyl alcohol vapors in water to form an aqueous solution of tertiary butyl alcohol, charging said aqueous solution of tertiary butyl alcohol to a distillation column and separating it therein at a liquid reflux ratio of about one-half to one at an elevated temperature of about 200° to about 400° F. and pressure of about 110 to about 160 psia into a lighter tertiary butyl alcohol fraction and a heavier water fraction, returning a portion of the liquified tertiary butyl alcohol to said vacuum distillation column as reflux, reacting the remainder of the liquified tertiary butyl alcohol with methanol to provide a methyl tertiary butyl ether reaction product comprising methyl tertiary butyl ether, unreacted tertiary butyl alcohol, unreacted methanol and water, and fractionating the methyl tertiary butyl ether reaction product in a methyl tertiary butyl ether distillation zone to provide distillation fractions including a methyl tertiary butyl ether product fraction and a tertiary butyl alcohol fraction.

7. A method as in claim 6 wherein said vacuum distillation column is operated under distillation conditions including a top temperature of about 130° to about 140° F., a bottoms temperature of about 160° to about 170° F., and a pressure of about 3 to about 10 psia.

8. In a method wherein tertiary butyl hydroperoxide is reacted with propylene in a first reaction zone to provide a first reaction product comprising by-products boiling below tertiary butyl alcohol, unreacted propylene, propylene oxide, tertiary butyl alcohol, unreacted tertiary butyl hydroperoxide, and by-products boiling above tertiary butyl alcohol, wherein said tertiary butyl hydroperoxide reaction product is charged to a first distillation column and separated therein into a first lighter distillation fraction comprising propylene and propylene oxide and a second heavier distillation fraction comprising tertiary butyl alcohol, unreacted tertiary butyl hydroperoxide, and reaction products boiling below tertiary butyl alcohol, the improvement which comprises:

charging said second heavier distillation tertiary butyl alcohol fraction to a vacuum distillation column operatively connected with a vacuum pump and separating said second heavier distillation fraction therein at subatmospheric pressure into a vented vaporized overhead tertiary butyl alcohol fraction and a lower boiling liquid fraction comprising unreacted tertiary butyl hydroperoxide, and reaction by-products boiling below tertiary butyl alcohol, condensing said vaporized overhead fraction to obtain a liquefaction product comprising a minor amount of vaporized tertiary butyl alcohol and a major amount of a liquified tertiary butyl alcohol, charging said condensed overhead fraction to a reflux drum, removing the liquified tertiary butyl alcohol from said reflux drum, and splitting it to provide a reflux stream for said vacuum distillation column and a recovered liquified tertiary butyl alcohol stream, venting said minor amount of vaporized tertiary butyl alcohol from said reflux drum through a vent line and dissolving the tertiary butyl alcohol in the vapors in the vent line with water to form an aqueous solution of tertiary butyl alcohol in water, charging said aqueous solution of tertiary butyl alcohol to a distillation column and separating it therein at a liquid reflux ratio of about one-half to one at an elevated temperature of about 200° to about 400° F. and pressure of about 110 to about 160 psia into a lighter tertiary butyl alcohol fraction and a heavier water fraction, further venting the remainder of said vapors to said vacuum pump, reacting said liquified tertiary butyl alcohol with methanol in a second reaction zone to provide a second reaction product comprising methyl tertiary butyl ether, unreacted methanol, unreacted tertiary butyl alcohol and water, fractionating said second reaction product in a third atmospheric distillation column to provide a lighter methyl tertiary butyl ether product fraction and a heavier third fraction, fractionating said third heavier fraction together with said aqueous solution of tertiary butyl alcohol in a fourth atmospheric distillation column to provide a lighter tertiary butyl alcohol fraction and a heavier fourth fraction, and fractionating said fourth heavier fraction in a fifth atmospheric distillation column to provide a lighter methanol product fraction and a heavier water fraction.

9. A method as in claim 8 wherein said vacuum distillation column is operated under distillation conditions including a top temperature of about 130° to about 140° F., a bottoms temperature of about 160° to about 170° F., and a pressure of about 3 to about 10 psia.

* * * * *